United States Patent [19]

Hess et al.

[11] Patent Number: 5,114,973

[45] Date of Patent: May 19, 1992

[54] METHOD FOR TREATING AUTOIMMUNE DISEASE USING SUCCINYLACETONE

[75] Inventors: Richard A. Hess, Bethesda; R. Michael Blaese, Rockville, both of Md.

[73] Assignee: The United States of America as represented by the Department of Health and Human Services, Washington, D.C.

[21] Appl. No.: 191,067

[22] Filed: May 6, 1988

[51] Int. Cl.$^5$ .............................................. A61K 31/19
[52] U.S. Cl. ...................................... 514/557; 514/885
[58] Field of Search ....................... 514/557, 574, 885

[56] References Cited

U.S. PATENT DOCUMENTS 4,670,467  6/1987  Hess et al. ........................... 514/885

OTHER PUBLICATIONS

Paul, Fundamental Immunology, 1984, Raven Press, N.Y. pp. 312-313 and 777.
Stites et al, Basic and Clinical Immunology 1984 p. 274, 408 and 409, Lange Med. Pub.
Middleton et al., Allergy vol. 2, 1983 p. 1384-1385, C. V. Mosby Co.
Theodore et al, Clinical Allergy and Immunology of the Eye 1983 p. 106-108, Williams & Wilkins Press.
Nussenblat et al, Uveitis, 1989, pp. 38-46.
Bach et al, Immunology 1982 pp. 422-424 and 545-546.
Nussenblatt et al., Chem. Abst. 102(17):142909b (1985).
Tschudy et al., Chem. Abst. 96(25):210579d (1982).

*Primary Examiner*—Douglas W. Robinson
*Assistant Examiner*—Zohreh A. Fay
*Attorney, Agent, or Firm*—John E. Tarcza

[57] ABSTRACT

The invention is a method of modulating or controlling autoimmune disease in a host. The method includes the step of administering to the diseased host a pharmaceutical effective amount of succinylacetone. The pharmaceutically effective amount of succinylacetone is desirably infused by an osmotic minipump in order to modulate the effects of autoimmune disease in the host.

14 Claims, 3 Drawing Sheets

METHOD FOR TREATING AUTOIMMUNE DISEASE USING SUCCINYLACETONE

BACKGROUND OF THE INVENTION

1. Field of the Invention

The invention relates generally to methods of treatment for autoimmune diseases. Specifically, the invention relates to methods of treatment for autoimmune diseases using succinylacetone.

2. Description of Related Art

Autoimmune disease is an inflammation triggered by an organism's reactivity to its own tissue. The search for pharmaceutical compositions and methods for treating this disease has been aided by the use of animals in which an experimental model of the disease has been developed. One such disease developed in laboratory animals is known as "experimental autoimmune uveitis" or "EAU." Successful methods for treating this autoimmune disease are useful for treating other autoimmune diseases.

Experimental autoimmune uveitis (EAU) is a T cell dependent model of ocular inflammation which can be induced in Lewis rats by footpad immunization of bovine retinal S-antigen in complete Freund's adjuvant. Retinal S-antigen is a 48K protein derived from the photoreceptors of the retina. Retinal S-antigen functions in phototransduction. The disease model can be transferred by a specific T-cell line but is not transferred by serum. When induced by active immunization, clinical inflammation begins 10 to 12 days after footpad injection. Low levels of antibody can be detected by day 7 after immunization and the popliteal lymphocyte proliferative response peaks at day 10. The inflammation occurs in the photoreceptors of the retina and in the pineal gland, both of which contain S-antigen. The ocular inflammation is characterized by photoreceptor cell loss followed by a more diffuse retinal destruction. The inflammation resolves in 7 to 10 days leaving an atrophic retina with glial remnants and does not spontaneously recur.

This experimental disease is a useful model to study the development and modulation of human ocular inflammation, because both disease conditions respond in approximately the same manner to pharmaceutical compositions and methods of treatment. For example, cyclosporine A has been helpful in regulating both ocular inflammation in experimental animals as well as human uveitis of probable autoimmune origin. Experimental autoimmune uveitis can be inhibited by cyclosporine if the drug is administered on or before day 7 after immunization. However, cyclosporine nephrotoxicity limits the use of this agent in uveitis and other autoimmune disease. Cyclosporine at a dose of 10 mg/kg daily will suppress experimental autoimmune uveitis at day 14 when started on day 0 or day 7 and there is a late relapse of inflammation if the drug is stopped. The development of other strategies for immune modulation of human autoimmune disease is desirable.

Succinylacetone (4,6-dioxoheptanoic acid) is an irreversible inhibitor of the second enzyme of the heme biosynthetic pathway, delta-amino levulinic acid dehydrase (ALAD). Although initial studies with this compound focused on its ability to inhibit the growth of erythroleukemic cells, through inhibition of heme biosynthesis, it is also capable of impairing the growth of other tumors by a mechanism independent of heme biosynthesis. This activity is disclosed in the article, Tschudy et al., "Growth Inhibitory Activity of Succinylacetones: Studies with Walker 256 Carcinosarcoma" Oncology 40:148 (1983), hereby incorporated by reference. In spite of the ability of succinylacetone to initially inhibit growth of the Walker 256 tumor, continuous treatment with succinylacetone actually enhanced allogeneic tumor growth in rats. This compound is also active in suppressing rat antibody responses to sheep red blood cells in vivo and in inhibiting mitogen and antigen responses by human lymphocytes in vitro. This characteristic of the compound is disclosed in Tschudy et al., "Immunosuppressive Activity of Succinylacetone" J. Lab & Clin. Medicine 99(4):526 (1982), hereby incorporated by reference.

Succinylacetone was initially believed to have anti-tumor activity via its irreversible inhibition of delta-ALA dehydrase and thus heme biosynthesis. However, further studies showed it was capable of inhibiting the growth of tumors that did not exhibit high levels of heme synthesis and, that prolonged administration resulted in enhanced tumor allograft growth, via an immunosuppressive effect. In spite of the potent effects of succinylacetone, one month of treatment does not demonstrate significant histopathologic abnormalities in any non-lymphoid organ. There is 12% decrease in hematocrit and a 20% decrease in hemoglobin due to suppression of heme production. This decrease in hemoglobin is only 40% of what would be expected if there was total inhibition of heme production.

Succinylacetone has been successfully used to totally inhibit graft vs host disease (GVHD) in allogeneic bone marrow transplantation. In spite of its strong effects on heme synthesis and immune function, succinylacetone does not interfere with engraftment or hematopoietic reconstitution. After one month treatment, there is only a minor depression of hemoglobin and lymphocytes in the blood and these parameters normalized when the drug was stopped. The animals treated by succinylacetone gain weight and no toxicity to other organ systems is seen.

U.S. Pat. No. 4,670,467 to Hess et al., hereby incorporated by reference, discloses a method of controlling graft versus host reaction. This method uses succinylacetone to treat or control this disease which results from bone marrow transplantation. This disclosure, as well as the two disclosures discussed above, do not suggest any method of treatment for autoimmune disease.

The industry is lacking a method for suppressing autoimmune disease. Such a method would also be desirable in modulating the effects of experimental autoimmune uveitis.

SUMMARY OF THE INVENTION

The invention is a method of modulating or controlling autoimmune disease in a host. The method includes the step of administering to the diseased host a pharmaceutical effective amount of succinylacetone. The pharmaceutically effective amount of succinylacetone must be sufficient to modulate the effects of autoimmune disease in the host.

DETAILED DESCRIPTION OF THE INVENTION

Figure 1:
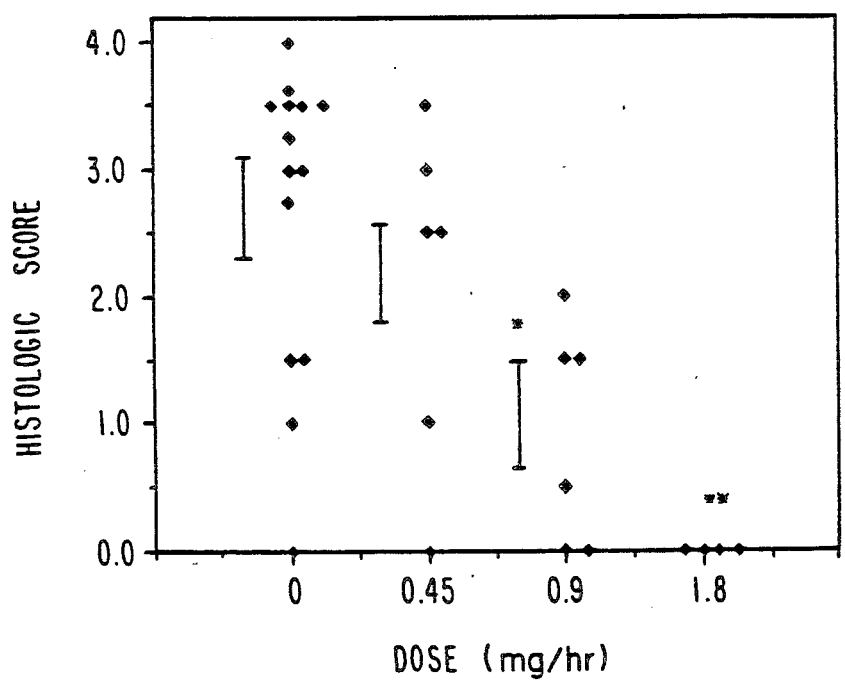
FIG. 1 illustrates that succinylacetone therapy decreases the histologic inflammation in experimental autoimmune uveitis in a dose related manner in animals treated from day 7 to 14 ($p < 0.004$ $p < 0.0001$).

The invention is a method for treating autoimmune uveitis and, thereby, autoimmune uveitis in hosts such as mammals. Succinylacetone is a potent inhibitor of experimental autoimmune uveitis. The compound or drug is capable of suppressing ocular inflammation, not only when given at the time of immunization, but also when initiated 7 days later, at a time when low levels of antibody to retinal S-antigen can usually be detected and the immune response has begun. Lymphocyte proliferative responses demonstrate a slight enhancement at intermediate drug dosages and marked suppression at higher doses whereas serum antibody levels are decreased only at higher dosages.

The effects of succinylacetone on the development of S-antigen induced experimental autoimmune uveitis in the rat is described as an example of the invention. Succinylacetone totally suppresses experimental autoimmune uveitis at day 14 when animals are treated with a constant infusion of 1.80 mg/hr by an osmotic minipump. Three intervals of treatment with this dose rate are used on day 0 to 7, day 7 to 14 or day 0 to 14. Regardless of dosage interval, suppression of disease is complete. There is a significant inhibition of S-antigen induced lymphocyte proliferative responses in cells from popliteal lymph nodes ($p < 0.009$) as well as a significant decrease of S-antigen antibody production. Animals treated with S-antigen at a rate of 0.90 mg/hr or 0.45 mg/hr develop experimental autoimmune uveitis in a dose related fashion. Animals treated with 1.8 mg/hr from day 7 to 14, but killed at day 30 have 100% breakthrough of disease. Succinylacetone inhibits the expression of experimental autoimmune uveitis and significantly suppress the immune response to S-antigen. However, once therapy is discontinued the high incidence of breakthrough suggests a reversible noncytotoxic mechanism of immune modulation.

Succinylacetone appears to be as potent an immunosuppressive agent as cyclosporine A. Succinylacetone offers the additional advantage of a low molecular weight and high water solubility which may facilitate permeability across the blood retinal barrier. As a result the compound can be administered in a wide range of therapeutically effective doses for the treatment of autoimmune diseases. The compound can produce a therapeutic response from about 2.5 to about 25 mg per kilograms of body weight per hour. A more desirable dosage range is from about 5 to about 15 mg per kilograms of body weight per hour. The preferred dosage is 10 mg per kilogram of body weight per hour. These dosages can be expected to vary between various host species including various mammals such as humans.

The dose response data for succinylacetone demonstrates a fairly narrow range of efficacy and toxicity. A 50% increase in the drug over the optimal dose leads to weight loss whereas a 50% decrease leads to the development of autoimmune uveitis. However, at these lower doses the severity of inflammation is still significantly less than in control animals. It is interesting to note the slight increase in antigen specific lymphocyte proliferation in animals treated with 0.9 and 0.45 mg/hr compared with untreated animals. This represents a delay in the kinetics of the development of antigen specific lymphocytes. It has been previously shown that untreated animals immunized with S-antigen have a peak in lymph node proliferative response at day 11 and that cyclosporine delays this peak. It is probable that a similar mechanism of delay is occurring in this invention in the animals that received lower doses. This accounts for the slight increase in response from animals killed 14 days after immunization. The higher doses of succinylacetone totally suppress this response.

The immunosuppressive effect of succinlyacetone is via an undefined mechanism. The data obtained in the inhibition of GVHD in bone marrow transplantation, such as that discussed above for the Hess patent, suggests that there is a cytostatic, but not cytotoxic action on cellular growth. This is because engraftment occurs and immune function returns. The data of this invention suggests a reversible mechanism of cellular action because of the delayed relapses of inflammation or that the antigen persist in the animal beyond the treatment period and then causes a response. The structure of succinylacetone does not suggest a mechanism of action and it can be the first of a unique group of cellular growth inhibitors. The immune system appears to be most sensitive to the effects of this drug. Its activity is not restricted to lymphocytes, since in vitro it also inhibits the growth of fibroblasts as well as tumor cells. The lack of total specificity for the immune system of succinylacetone does not preclude its potential as a useful immunosuppressive agent in both organ transplantation and autoimmune disease. The properties, low molecular weight, water solubitiy, and a synthesis which does not depend on a biologic system suggest significant advantages for regulation of the immune response in human disease.

EXAMPLE

The following example demonstrates the preferred embodiment of the invention. The following methods and materials were used to conduct the experiment.

Induction of the experimental autoimmune uveitis was initiated in female Lewis rats that were 6 to 8 weeks old. The rats weigh 175 to 200 grams. Bovine retinal S-antigen was prepared as previously described. Animals were immunized by injecting into each hind footpad 0.1 cc of an emulsion containing 15 ug of S-antigen in phosphate buffered saline (PBS) mixed with an equal volume of complete Freund's adjuvant which is commerically available from Gibco, Grand Island, NY and which was augmented with HJ37Ra Mycobacterium tuberculosis to a concentration of 2.5 mg/ml. The animals were killed by $CO_2$ inhalation fourteen or thirty days after immunization. In those animals killed at day 14, cardiac puncture to obtain blood was also performed using $CO_2$ induced anesthesia. The blood was allowed to clot overnight in the refrigerator. The serum was removed and stored at $-25°$ C. In addition, draining popliteal lymph nodes and pineal glands were removed from day 14 animals.

Treatment with succinylacetone is as follows. Crystalized succinylacetone was obtained from Colorado Biotechnoloqy, Casper, Wyoming. A sterile solution was prepared in Phosphate buffered saline and neutralized with 5 N NaOH to pH 7.4. The drug was delivered by miniosmotic pumps 2ML2, which are commerically available from Alza Corp., Palo Alto, California for a two week administration or 2MLI for a one week administration. Solutions of 100 mg/ml, 200 mg/ml, 400 mg/ml and 600 mg/ml were used. Pumps were held submerged in sterile Phosphate buffered saline during the short interval or less than 30 minutes between pump filing and pump implantation into the rats.

The animals were anesthesized with a combination of 10 mg of Ketamine and 1 mg of Rompun IM and supplemented with the same mixture as needed. A skin area of the mid-back of the rat was shaved with electric clippers and cleaned thoroughly with 70% ethyl alcohol. A transverse 2.5 to 3.0 cm incision was made and the area caudal to the incision was undermined to accommodate the pump.

Forty-three animals were followed for 14 days after immunization. Twenty-nine animals received pumps containing succinylacetone as follows: Five animals received a 600 mg/ml pump for days 0 to 14; 4 animals received 400 mg/ml pump for day 0 to 14; 4 animals received a 400 mg/ml pump for day 0 to 7; 4 animals received a 400 mg/ml pump for day 7 to 14; 6 animals were given 200 mg/ml day 7 to 14; and 6 animals received 100 mg/ml from day 7 to 14. The control group consisted of 14 rats which were immunized as above for the development of experimental autoimmune uveitis and were implanted with ALZET miniosmotc pumps containing normal saline. All animals were sacrificed at day 14. An additional 6 animals were immunized with S-Antigen and received pumps containing 400 mg/ml from day 7 to 14 and were then killed on day 30.

Ocular and pineal gland histology was examined as follows. The eyes and pineal glands were removed and fixed in 10% formalin, embedded in paraffin, sectioned, cleared and then stained with hematoxylin and eosin. The presence of ocular inflammation as defined by the presence of intraocular lymphocytes and photoreceptor destruction was read by an impartial observer, using previously published criteria grading experimental autoimmune uveitis from 0 to 4+. The ocular grading in both eyes of one animal was averaged and used to indicate the incidence of experimental autoimmune uveitis. Pineal inflammation was considered present if lymphocyte infiltration was observed in the pineal gland by the impartial observer.

The lymphocyte proliferation assay was made as follows. Cultures were performed on animals from each group killed at day 14. The cells from the popliteal lymph nodes of each animal were harvested by gentle teasing and cultured at a concentration of $1\times 10^6$ cells/ml in 96 well culture plates, that are commerically available from Costar, Cambridge, MA. Each contained 200,000 cells in 0.2 ml culture medium consisting of 0.2 cc of RPMI-1640, which is commercially available from Gibco, Grand Island, NY, supplemented with 10% fetal calf serum, which is commerically available from Hyclone, Logan, Utah and 100 U/ml of penicillin and 10 ug/ml of streptomycin. Quadruplicate culture wells of cells with media, Concanavalin A (Con A) 1 ug/well and S-antigen 5 ug/well were done on each animal. The cultures were incubated at 37° C. in 5% $CO_2$ for 3 days, pulsed with 1 uCi of 3H-thymidine from New England Nuclear, Boston, MA, and incubated for an additional 16 hours. The plates were then harvested on a Mash II harvester and counted in a scintillation counter, the quadruplicate well counts were averaged. A stimulation index (S.I.) was calculated for each set of quadruplicates by dividing the experimental mean by the control mean for each animal.

Elisa assay for anti-S-antigen antibody were then performed. This assay used 96 well flat bottomed plates from Costar, Cambridge, MA were coated with 50 ul of a 8 ug/ml solution of S-antigen in phosphate buffered saline and incubated for 1 hour at 37° C. The plates were then washed 3 times in 1% bovine serum albumin or in phosphate buffered saline, incubated with bovine serum albumin in phosphate buffered saline for 1 hour at 37° C., emptied, and stored at 4° C. A dilution of 1:2500 of serum in phosphate buffered saline was used. 50 ul of serum were incubated at 37° C. in the precoated plated for one hour. The plates were then washed three times with 0.1% Tween from Sigma, St. Louis, MO, in phosphate buffered saline, incubated at 37° C. with 50 ul of a 1:2000 dilution of goat anti-rat igG having both heavy and light chain from Kirkegaard and Pery, Gaithersburg, MD, washed three times with Tween and phosphate buffered saline, incubated with 50 ul each of Peroxidase Substrate solutions A and B from Kirkegaard and Perry and incubated for 15 minutes. A positive and negative standard were run on each plate and the optical density was read on a Minireader II Elisa reader from Dynatech. Alexandria. VA.. All samples were run in duplicate on a single day. The optical densities of the samples were normalized to the standard for the purpose of comparison. There was less than 5% variation between the optical density of the standards of the Elisa plates.

The data were analyzed utilizing the Statistical Analysis System Cary, NC. The Fisher's Exact test was used for $2\times 2$ comparisons of categorical data. The Student t test was used to compare continuous data between the treatment groups. All data is reported as mean ±1 S.E.M. The results of this Example are presented in Table 1.

TABLE 1

The Effect of Succinylacetone on the Development of Experimental Autoimmune Uveitis and Pinealitis

| Succinylacetone (mg/hr) | Treatment Duration | # Animals with EAU/Total | # Animals with Pinealitis/Total |
|---|---|---|---|
| Untreated | — | 13/14 | 8/8 |
| 2.7 | 0–14 | 0/2 | — |
| 1.8 | 0–14 | 0/4* | 0/4* |
| 1.8 | 0–7 | 0/4* | 0/4* |
| 1.8 | 7–14 | 0/4* | 0/4* |
| .9 | 7–14 | 4/6 | — |
| .45 | 7–14 | 5/6 | — |

*p < .004 compared to control (Fisher Exact Test)
3 died due to drug

Table 1 summarizes the histologic incidence of ocular and pineal inflammation in control animals and in animals treated with succinylacetone. Thirteen of 14 untreated animals developed severe experimental autoimmune uveitis with significant retinal destruction and 8 of 8 animals examined developed pinealitis. Treatment with succinylacetone at 1.8 mg/hr totally suppressed the development of experimental autoimmune uveitis and pinealitis even when delivered only from day 0 to 7 as well as for days 7 to 14 or 0 to 14. Lower doses of succinylacetone resulted in partial suppression with less destructive inflammation in the animals that did develop experimental autoimmune uveitis. The dose of 2.7 mg/hr for 14 days resulted in marked weight loss or mortality.

FIG. 1 shows dose response data for the severity of the intra-ocular inflammation in animals treated from day 7 to 14. A grade of 4 indicates total retinal destruction whereas a grade of 1 indicates mild inflammation with patchy photoreceptor loss. The severity of inflammation is significantly reduced in both the 1.8 mg/hr (0 ±)) and 0.9 mg/hr (0.92±0.35) group compared with control animals (2.7±0.32 (p <0.004 respectively).

Figure 2A:
FIG. 2 illustrates retinal inflammation in untreated experimental autoimmune uveitis (a) and no inflammation in an animal treated with 1.8 mg/hr of succinylacetone from day 7 to 14 (b) (H&E 200x)
Figure 2B:

FIG. 2 compares the histologic inflammatory response in the eye of an untreated animal with the lack of inflammation in an animal treated with succinylacetone from day 7 to 14 at a rate of 1.8 mg/hr.

Figure 3:
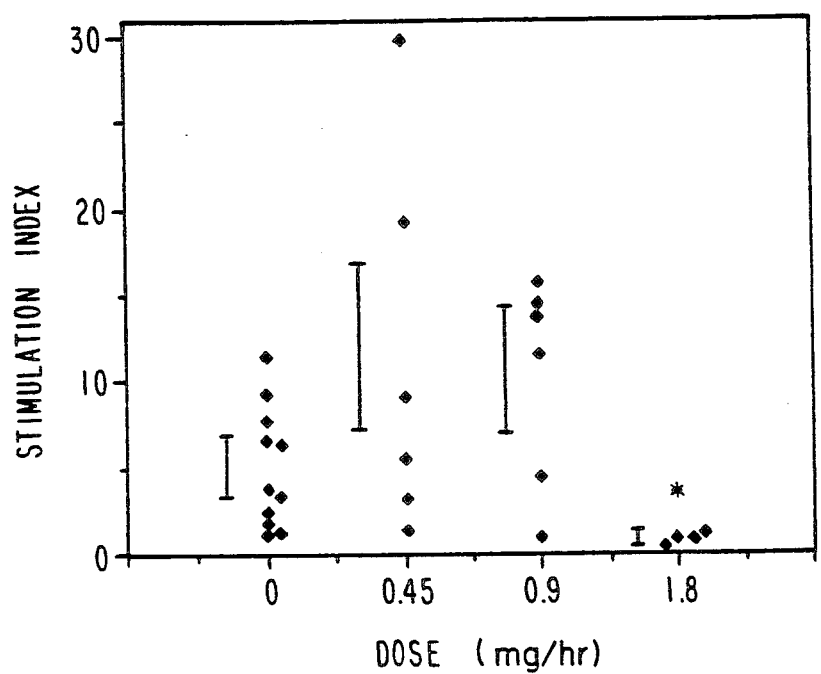
FIG. 3 illustrates S-antigen lymphocyte mitogenesis at day 14 in lymphocytes from animals treated from day 7 to 14 succinylacetone ($p < 0.009$).

FIG. 3 demonstrates the lymph node proliferative response to S-antigen in animals treated from day 7 to 14. The stimulation index response of animals that received 0.45 (11.4±4.5) and 0.9 mg/hr (10.1±2.4) is higher than untreated animals (5.4±1.0), but the difference is not statistically significant. The 1.8 mg/hr (0.84±0.13) animals have a significantly lower response (p <0.009). In addition, animals treated with 1.8 mg/hr from day 0 to 14 or 0 to 7 also showed significant decrease in lymphocyte response. The mean for these two groups was 0.7±0.06 and 0.74±0.08 (p <0.009) compared to untreated animals.

Figure 4:
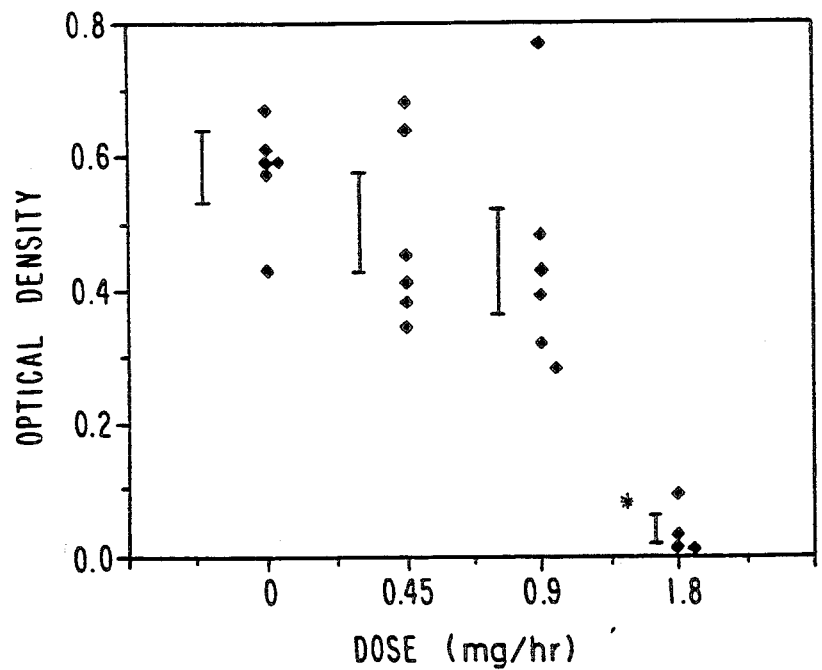
FIG. 4 illustrates anti-S-antigen antibody response in animals treated with succinylacetone from day 7 to 14 ($p < 0.004$).

FIG. 4 illustrates the alteration in S-antigen antibody (IgG H and L chain) production in animals treated with succinylacetone from day 7 to 14. The Elisa O.D. corresponding to serum antibody on day 14 in untreated animals was (0.58±0.03). Significant reduction was only seen with the 1.8 mg/hr. dose (0.03±0.02) (p <0.004). Additionally, the mean O.D. using the S-antigen Elisa on sera from animals treated with 1.8 mg/hr from day 0 to 14 or 0 to 7 was 0 and 0.003±0.1 respectively (p <0.004). This corresponds to at least a 50 fold decrease in antibody titer.

Treatment of animals from day 7 to 14 with a delay in killing the animals until day 30 result in a 100% incidence of histologic disease on both the pineal gland and the retina with a score of 2.9±0.2, indicating marked retinal damage.

The results of this Example demonstrate total suppression of experimental autoimmune uveitis at a dose of 1.8 mg/hr. The ability to suppress the ocular inflammation when the drug is started on day 7 implies that the immunosuppressive activity can occur even after the initial steps of immunization have occurred. In addition, the effect of therapy when given from day 0 to 7 suggests that the immunosuppressive activity persists for several days after it is discontinued. By contrast, the 100% incidence of inflammation at day 30 when the drug was given from day 7 to 14 suggests reversibility of the immunosuppressive action. This was also suggested by the normal immunologic reconstitution in rats that received bone marrow transplants, implying reversibility of the suppressive effects of succinylacetone.

What is claimed is

1. A method of treating autoimmune disease in a host in need thereof comprising:
    administering to said host a therapeutically effective amount of succinylacetone sufficient to modulate the effects of said autoimmune disease in said host.

2. The method of claim 1 wherein said therapeutically effective amount of succinylacetone is from about 2.5 to about 25 mg per kilogram of body weight per hour.

3. The method of claim 2 wherein said therapeutically effective amount of succinylacetone is from about 5 to about 15 mg per kilogram of body weight per hour.

4. The method of claim 3 wherein said therapeutically effective amount of succinylacetone is is about 10 mg per kilogram of body weight per hour.

5. The method of claim 1 wherein said host is a mammal.

6. The method of claim 5 wherein said host is a Lewis rat.

7. A method of treating autoimmune uveitis in a host comprising administering to said host a therapeutically effective amount of succinylacetone, wherein said therapeutically effective amount is sufficient to modulate the effects of autoimmune uveitis in said host.

8. The method of claim 7 wherein said therapeutically effective amount of succinylacetone is from about 2.5 to about 25 mg per kilogram of body weight per hour.

9. The method of claim 8 wherein said therapeutically effective amount of succinylacetone is from about 5 to about 15 mg per kilogram of body weight per hour.

10. The method of claim 9 wherein said therapeutically effective amount of succinylacetone is is about 10 mg per kilogram of body weight per hour.

11. The method of claim 7 wherein said host is a mammal.

12. The method of claim 11 wherein said host is a Lewis rat.

13. The method of claim 7 wherein said succinylacetone is continuously infused by an osmotic minipump.

14. The method of claim 7 wherein said autoimmune uveitis is experimental autoimmune uveitis.

* * * * *